US00PP28523P3

(12) United States Plant Patent
Holtmaat

(10) Patent No.: US PP28,523 P3
(45) Date of Patent: Oct. 10, 2017

(54) ***ECHINACEA* PLANT NAMED 'ECHGOL243'**

(50) Latin Name: *Echinacea hybrida*
Varietal Denomination: Echgol243

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 58 days.

(21) Appl. No.: 14/756,661

(22) Filed: Sep. 29, 2015

(65) Prior Publication Data

US 2017/0094881 P1 Mar. 30, 2017

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

AB Cultivars Breeding for Better Gardens retrieved on Jan. 19, 2017, retrieved from the Internet at <http://www.ab-cultivars.com/en/assortment/echinacea-golden-skipper/> one page.*
Upov Pluto Plant Variety Database Jan. 17, 2017, retrieved on Jan. 19, 2017, retrieved on retrieved from the Internet at <www.3.wipo.int/pluto/user/en/index.jsp> one page.*

* cited by examiner

*Primary Examiner* — June Hwu
(74) *Attorney, Agent, or Firm* — C. A. Whealy

(57) ABSTRACT

A new and distinct cultivar of *Echinacea* plant named 'Echgol243', characterized by its upright and relatively compact plant habit; moderately vigorous growth habit; freely branching habit; strong flowering stems; numerous large single-type inflorescences with bright golden yellow-colored ray florets and dark orange-colored receptacle spines; and good garden performance.

2 Drawing Sheets

Botanical designation: *Echinacea hybrida.*
Cultivar denomination: 'ECHGOL243'.

BACKGROUND OF THE INVENTION

The present invention relates to a new and distinct cultivar of *Echinacea* plant, botanically known as *Echinacea hybrida*, and hereinafter referred to by the name 'Echgol243'.

The new *Echinacea* plant is a product of a planned breeding program conducted by the Inventor in Zuidwolde, The Netherlands. The objective of the breeding program is to develop new freely flowering and relatively compact *Echinacea* plants with unique and attractive ray floret coloration.

The new *Echinacea* plant originated from a cross-pollination in July, 2012 in Zuidwolde, The Netherlands of *Echinacea hybrida* 'Cleopatra', disclosed in U.S. Plant Pat. No. 24,631, as the female, or seed, parent with *Echinacea hybrida* 'Julia', disclosed in U.S. Plant Pat. No. 24,629, as the male, or pollen, parent. The new *Echinacea* plant was discovered and selected by the Inventor as a single flowering plant from within the progeny of the stated cross-pollination grown in a controlled greenhouse environment in Zuidwolde, The Netherlands in July, 2013.

Asexual reproduction of the new *Echinacea* plant by in vitro meristem culture in a controlled environment in Zuidwolde, The Netherlands since October, 2013 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Echgol243'. These characteristics in combination distinguish 'Echgol243' as a new and distinct *Echinacea* plant:

1. Upright and relatively compact plant habit.
2. Moderately vigorous growth habit.
3. Freely branching habit.
4. Strong flowering stems.
5. Numerous large single-type inflorescences with bright golden yellow-colored ray florets and dark orange-colored receptacle spines.
6. Good garden performance.

Plants of the new *Echinacea* can be compared to plants of the female parent, 'Cleopatra'. Plants of the new *Echinacea* differ from plants of 'Cleopatra' primarily in ray floret color as ray florets of plants of 'Cleopatra' are soft yellow in color. In addition, plants of 'Cleopatra' are more freely branching than plants of the new *Echinacea.*

Plants of the new *Echinacea* can be compared to plants of the male parent, 'Julia'. Plants of the new *Echinacea* differ from plants of 'Julia' primarily in ray floret color as ray florets of plants of 'Julia' are orange in color. In addition, plants of 'Julia' are more freely branching than plants of the new *Echinacea*.

Plants of the new *Echinacea* can be compared to plants of *Echinacea purpurea* 'Avalanche', disclosed in U.S. Plant Pat. No. 18,597. In side-by-side comparisons conducted in Zuidwolde, The Netherlands, plants of the new *Echinacea* differed primarily from plants of 'Avalanche' in the following characteristics:

1. Plants of the new *Echinacea* were shorter than plants of 'Avalanche'.
2. Plants of the new *Echinacea* were not as freely branching as plants of 'Avalanche'.
3. Plants of the new *Echinacea* and 'Avalanche' differed in ray floret color as ray florets of plants of 'Avalanche' were white in color.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Echgol243' grown in ground beds in an outdoor nursery and placed in a 17.5 cm by 22 cm container for the photograph.

The photographs on the second sheet are close-up views of a typical inflorescence (upper photograph) and the upper surface of a typical leaf (lower photograph) of 'Echgol243'.

DETAILED BOTANICAL DESCRIPTION

The aforementioned photographs and following observations and measurements describe plants grown during the summer in ground beds in an outdoor nursery in Zuidwolde, The Netherlands and under cultural practices typically used in commercial *Echinacea* production. During the production of the plants, day temperatures ranged from 18° C. to 32° C. and night temperatures ranged from 8° C. to 20° C. Plants were eight months old when the photographs and description were taken. In the following description, color references are made to The Royal Horticultural Society Colour Chart, 2007 Edition, except where general terms of ordinary dictionary significance are used.

Botanical classification: *Echinacea hybrida* 'Echgol243'.

Parentage:

*Female parent.*—*Echinacea hybrida* 'Cleopatra', disclosed in U.S. Plant Pat. No. 24,631.

*Male parent.*—*Echinacea hybrida* 'Julia', disclosed in U.S. Plant Pat. No. 24,629.

Propagation:

*Type.*—By in vitro meristem culture.

*Time to initiate roots, summer.*—About one week at temperatures about 25° C.

*Time to produce a rooted young plant, summer.*—About five weeks at temperatures about 21° C.

*Root description.*—Fine, fibrous; typically pale cream in color, actual color of the roots is dependent on substrate composition, water quality, fertilizer type and formulation, substrate temperature and physiological age of roots.

*Rooting habit.*—Freely branching; medium density.

Plant description:

*Plant form and growth habit.*—Herbaceous perennial; upright and relatively compact plant habit, narrow inverted triangle; freely branching habit with about 20 lateral branches developing per plant; moderately vigorous growth habit.

*Plant height.*—About 54.9 cm.

*Plant diameter or spread.*—About 43.3 cm.

*Lateral branches.*—Length: About 33.4 cm. Diameter: About 6 mm. Internode length: About 8.7 cm. Aspect: Erect to about 10° from vertical. Strength: Very strong. Texture: Densely pubescent; strigose; slightly rough. Color: Close to 144A.

Leaf description:

*Basal leaves.*—Arrangement: Alternate, simple. Length: About 14.9 cm. Width: About 6.4 cm. Shape: Ovate to narrowly ovate; slightly concave. Apex: Acute. Base: Attenuate. Margin: Entire to shallowly dentate; undulate. Texture and luster, upper and lower surfaces: Moderately pubescent, strigose; rough; moderately glossy. Venation pattern: Pinnate. Color: Developing leaves, upper surface: Slightly darker than 143A. Developing leaves, lower surface: Close to 137C. Fully expanded leaves, upper surface: Close to NN137A; venation, close to 145A. Fully expanded leaves, lower surface: Close to 147B; venation, close to 144C. Petioles, basal leaves: Length: About 6 cm. Diameter: About 4 mm. Height: About 4 mm. Strength: Strong, flexible. Texture and luster, upper surface: Glabrous except along the margins, sparsely pubescent; slightly glossy. Texture, lower surface: Glabrous; matte. Color, upper surface: Close to 145A; margins, close to NN137A. Color, lower surface: Close to 144C; margins, close to 147C.

*Cauline leaves.*—Arrangement: Alternate, simple. Length: About 9.3 cm. Width: About 2.7 cm. Shape: Ovate to narrowly ovate; slightly concave. Apex: Acute. Base: Attenuate. Margin: Entire to shallowly dentate; undulate. Texture and luster, upper and lower surfaces: Moderately pubescent, strigose; moderately glossy. Venation pattern: Pinnate. Color: Developing leaves, upper surface: Slightly darker than 143A. Developing leaves, lower surface: Close to 137C. Fully expanded leaves, upper surface: Close to NN137A; venation, close to 145A. Fully expanded leaves, lower surface: Close to 147B; venation, close to 144C. Petioles, cauline leaves: Length: About 5 mm. Diameter: About 3 mm. Height: About 3 mm. Strength: Strong, flexible. Texture and luster, upper surface: Glabrous except for along the margins, sparsely pubescent; slightly glossy. Texture, lower surface: Glabrous; matte. Color, upper surface: Close to 145A; margins, close to NN137A. Color, lower surface: Close to 144C; margins, close to 147C.

Inflorescence description:

*Appearance.*—Large single-type inflorescences with ray and disc florets arranged on a capitulum; inflorescences positioned upright above the foliar plane on mostly upright and strong peduncles.

*Flowering habit*.—Freely flowering habit with about 60 inflorescences developing per plant during the flowering season.

*Fragrance*.—Moderately fragrant; somewhat acidic, pleasant.

*Time to flower*.—In the garden, plants flower continuously from early July to late September in The Netherlands.

*Inflorescence longevity*.—Inflorescences maintain good substance for about three weeks on the plant; inflorescences persistent.

*Inflorescence buds*.—Height: About 2.5 cm. Diameter: About 3.7 cm. Shape: Flattened globular. Color: Involucral bracts, close to 144A to 144B; ray florets, close to between 151C and 154C.

*Inflorescence size*.—Diameter: About 10.5 cm. Depth (height): About 5.1 cm. Disc diameter: About 4.1 cm. Receptacle height: About 1.2 cm. Receptacle diameter: About 1.4 cm. Receptacle color: Close to NN155A.

*Ray florets*.—Quantity and arrangement: About 27 arranged in a single whorl at the base of the receptacle. Length: About 4.9 cm. Width: About 1.15 cm. Shape: Oblanceolate. Apex: Praemorse. Base: Cuneate. Margin: Entire. Texture, upper surface: Glabrous; velvety; longitudinally ridged. Texture, lower surface: Glabrous; longitudinally ridged. Luster, upper surface: Matte. Luster, lower surface: Slightly glossy. Aspect: Horizontal to drooping, about 20° from horizontal. Color: When opening, upper surface: Close to N25C. When opening, lower surface: Close to 18B. Fully opened, upper surface: Close to 25A; towards the base, tinged with close to 13A; color becoming closer to between 15A and 16A with development; with subsequent development, color becoming closer to 11B and 160B. Fully opened, lower surface: Close to 16B and 23D; color becoming closer to 8C with development; with subsequent development, color becoming closer to 150B to 150C.

*Disc florets*.—Quantity and arrangement: About 400 per inflorescence, spirally at the center. Length: About 1.15 cm. Diameter: About 2 mm. Shape: Tubular; proximally, 15% free, not fused. Apex: Acute. Base: Fused. Margin: Entire. Texture, inner and outer surfaces: Smooth, glabrous. Luster, inner and outer surfaces: Glossy. Color, when opening, inner and outer surfaces: Apex: Close to 144A to 144B. Mid-section: Close to 144C. Base: Close to 144A to 144B. Color, fully opened, inner and outer surfaces: Apex: Close to 144A to 144B. Mid-section: Close to 144C. Base: Close to 144A to 144B.

*Receptacle spines*.—Quantity: One per disc floret. Shape: Acicular. Apex: Acute. Base: Attenuate. Texture: Smooth, glabrous. Luster: Glossy. Color: Apex: Close to 23A. Mid-section: Close to 144A. Base: Close to 144C.

*Involucral bracts*.—Quantity per inflorescence: About 80 arranged in about four whorls. Length: About 8 mm. Width: About 2 mm. Shape: Ovate to narrowly ovate. Apex: Acute. Base: Cuneate. Margin: Entire. Texture, upper surface: Smooth, glabrous. Texture, lower surface: Moderately pubescent. Luster, upper and lower surfaces: Matte. Color, upper surface: Close to N137A. Color, lower surface: Close to 137C.

*Peduncles*.—Length: About 9.7 cm. Diameter: About 5 mm. Strength: Strong. Aspect: Upright to about 30° from vertical. Texture: Sparsely pubescent; strigose. Color: Close to 144A.

*Reproductive organs*.—Androecium (present on ray and disc florets): Quantity per floret: Five. Filament length: About 3 mm. Filament color: Close to 150D. Anther length: About 3 mm. Anther shape: Narrowly oblong. Anther color: Close to 200A. Pollen amount: Scarce. Pollen color: Close to 17A. Gynoecium (present only on disc florets): Quantity per floret: One. Pistil length: About 7.5 mm. Stigma shape: Decurrent, unequal. Stigma color: Close to 150B. Style length: About 6 mm. Style color: Close to 150D. Ovary color: Close to 157D. Seeds and fruits: Seed and fruit development have not been observed on plants of the new *Echinacea*.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Echgol243' as illustrated and described.

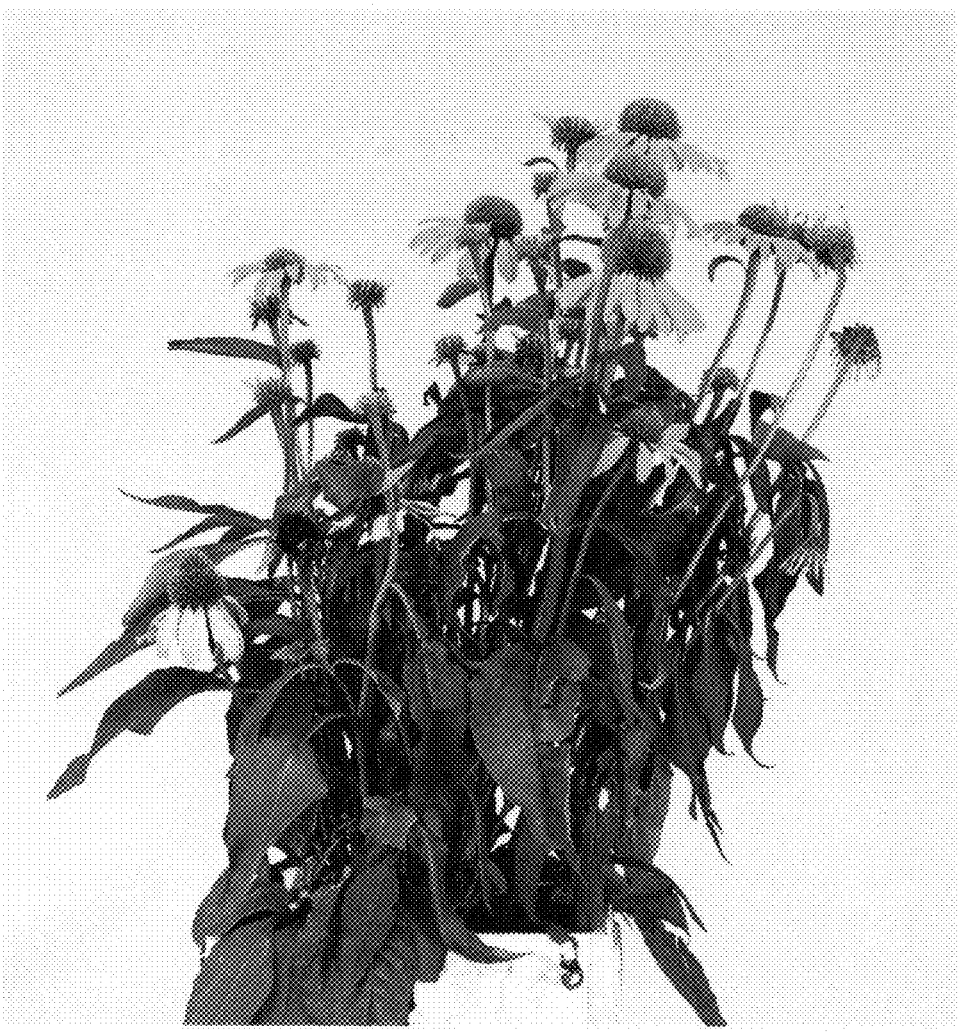

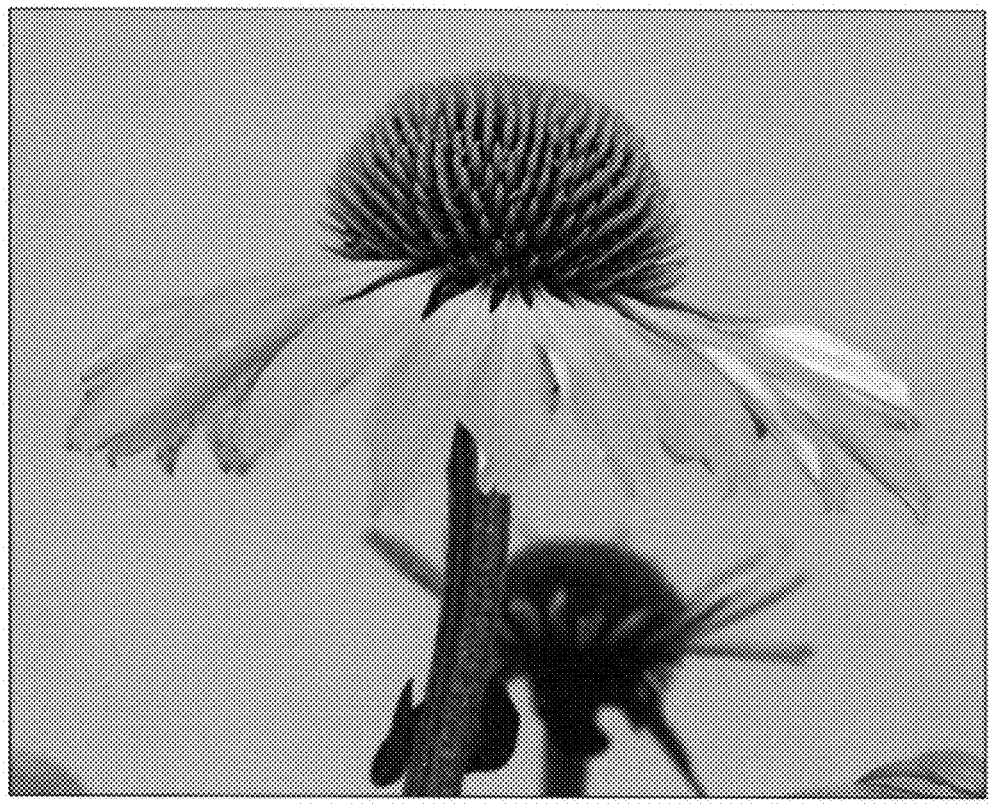
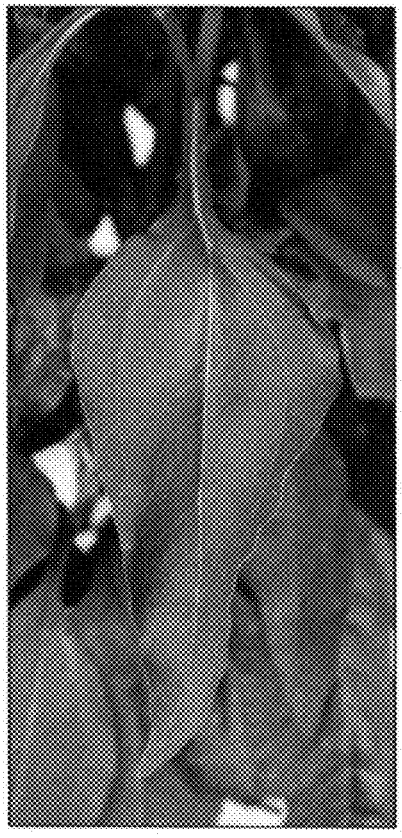

* * * * *